US00PP28338P3

(12) United States Plant Patent
Bradford et al.

(10) Patent No.: US PP28,338 P3
(45) Date of Patent: Aug. 29, 2017

(54) PEACH TREE NAMED 'RED PRINCESS II'

(50) Latin Name: *Prunus persica*
Varietal Denomination: Red Princess II

(71) Applicants: Lowell Glen Bradford, Le Grand, CA (US); Jon M. Quisenberry, Le Grand, CA (US)

(72) Inventors: Lowell Glen Bradford, Le Grand, CA (US); Jon M. Quisenberry, Le Grand, CA (US)

( * ) Notice: Subject to any disclaimer, the term of this patent is extended or adjusted under 35 U.S.C. 154(b) by 48 days.

(21) Appl. No.: 14/757,243

(22) Filed: Dec. 11, 2015

(65) Prior Publication Data

US 2017/0172034 P1 Jun. 15, 2017

(51) Int. Cl.
*A01H 5/08* (2006.01)

(52) U.S. Cl.
USPC ..... Plt./197

(58) Field of Classification Search
USPC ..... Plt./197
See application file for complete search history.

(56) References Cited

U.S. PATENT DOCUMENTS

| | | | |
|---|---|---|---|
| PP17,282 | P2 | 12/2006 | Bradford |
| PP17,750 | P2 | 5/2007 | Bradford |
| PP18,771 | P2 | 4/2008 | Bradford |

*Primary Examiner* — June Hwu

(57) ABSTRACT

The present invention relates to a new and distinct variety of peach tree, *Prunus persica*, broadly characterized by a medium to small size, weakly vigorous, hardy, self-fertile, productive and regular bearing tree. The variety blooms during the early season and requires about 300 chilling hours. The fruit matures under the ecological conditions described in mid May, with first picking on May 15, 2015. The fruit is uniform, large in size, acidic with traditional peach flavor, oblate in shape, clingstone in type, firm and non-melting in texture, yellow in flesh color, virtually full red in skin color, and has a bitter tasting kernel.

1 Drawing Sheet

Botanical classification: *Prunus persica.*
Variety denomination: 'RED PRINCESS II'.

BACKGROUND OF THE VARIETY

In a continuing effort to improve the quality of shipping fruits, we, the inventors, typically hybridize a large number of peach, nectarine, plum, apricot, and cherry seedlings each year. We also grow a smaller number of open pollinated seeds of each of these fruits, usually to capture recessive traits. The present invention relates to a new and distinct variety of peach tree, which has been denominated varietally as 'Red Princess II'.

In 2007 we made a first generation hybridization using 'Ivory Duchess' (U.S. Plant Pat. No. 17,282) peach as the selected seed parent and 'May Princess' (U.S. Plant Pat. No. 18,771) peach as the selected pollen parent. Upon reaching maturity the fruit of this hybridization was gathered, and the seeds were removed, cracked, stratified, germinated, and grown as seedlings on their own root in our greenhouse facility. Upon reaching dormancy we transplanted them to a cultivated area of our experimental orchard located near Le Grand, Calif., in Merced County (San Joaquin Valley). During the fruit evaluation season of 2011 we selected the present variety as a single tree from the group of seedlings described above. Subsequent to origination of the present variety of peach tree, we asexually reproduced it by budding and grafting in the experimental orchard described above, and such reproduction of plant and fruit characteristics were true to the original tree in all respects. The reproduction of the variety included the use of 'Nemaguard' (unpatented) rootstock upon which the present variety was compatible and true to type.

The present variety is similar to its seed parent, 'Ivory Duchess' (U.S. Plant Pat. No. 17,282) peach, by being self-fertile and by producing peaches that are mostly red in skin color, that are clingstone in type, that are large in size, and that ripen in the early season, but is quite distinguished from it by having reniform instead of globose leaf glands, by requiring less chilling hours, and by producing fruit that is yellow instead of white in flesh color, that is oblate instead of globose in shape, and that is non-melting instead of melting in texture.

The present variety is similar to its pollen parent, 'May Princess' (U.S. Plant Pat. No. 18,771) peach, by being self-fertile, by having a showy blossom, by blooming in the early season, by being fairly low in chilling requirement, by having reniform glands, and by producing peaches that are mostly red in skin color, yellow in flesh color, clingstone in type, oblate in shape, and non-melting in texture, but is quite distinguished from it by being only moderately vigorous and by producing fruit that is larger in size and that ripens about seventeen days later.

The present variety is most similar to 'Spring Princess' (U.S. Plant Pat. No. 17,750) peach by being self-fertile, by having a low chilling requirement, by having a large blossom, by blooming in the early season and by producing peaches that are mostly red in skin color, yellow in flesh color, oblate in shape, clingstone in type, large in size, and very good in flavor, but is distinguished therefrom by having a smaller and less vigorous tree, by having reniform instead of globose glands, and by producing fruit that is non-melting instead of melting in texture, that has a bitter instead of sweet kernel, and that ripens about five days later.

SUMMARY OF VARIETY

In summary, the present peach variety is characterized by a medium to small size, weakly vigorous, hardy, self-fertile, productive and regular bearing tree. The variety blooms during the early season and requires about 300 chilling hours. The fruit matures under the ecological conditions described in mid May, with first picking on May 15, 2015. The fruit is uniform, large in size, acidic with traditional peach flavor, oblate in shape, clingstone in type, firm and non-melting in texture, yellow in flesh color, virtually full red in skin color, and has a bitter tasting kernel.

DRAWING

The accompanying photograph consists of four whole fruits positioned to display the characteristics of the skin color and form, one sliced fruit to reveal the flesh and stone, typical leaves, and two insets depicting the flower buds and blossoms as they appear on the tree during the blooming season.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of firm ripe on May 20, 2015, on the original tree during its eighth growing season. The blossom and flower descriptions were made the previous blooming season. All major color code designations are by reference to the Inter-Society Color Council, National Bureau of Standards. Common color names are also used occasionally.

It is to be noted that the 2015 fruit season in California was very warm during the spring and the ripening times of almost all varieties were about twenty days earlier than other years.

PARENTAGE

Seed parent: 'Ivory Duchess' (U.S. Plant Pat. No. 17,282) peach.

Pollen parent: 'May Princess' (U.S. Plant Pat. No. 18,771) peach.

TREE

Size: Small, reaching and maintaining a height of 8' [2.44 m.] and a spread of 5' [1.52 m.] after eight growing seasons utilizing typical dormant pruning.

Vigor: Weak, responding below average to irrigation and fertilization. The variety grows about 2' [0.61 m.] of surplus top-growth during the spring and summer. The plant should be grown on a standard commercial rootstock for production purposes.

Growth: Spreading and dense.

Form: Pruned to a Central Leader type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Productive, thinning usually necessary.

Fertility: Self-fertile.

Bearing: Regular bearer, with no crop failures observed.

Chilling requirement: About 300 hours.

Leaf bud burst: Early, during the onset of flowering.

Trunk:

*Size*.—Slender, reaching a maximum diameter of 2⅞" [73 mm.] after the eighth growing season.

*Texture*.—Medium roughness.

*Bark color*.—A Grayish brown [61. gy.Br] and Light grayish brown [60. l.gy.Br] variegation with Light grayish yellowish brown [79. l.gy.yBr] crevices present.

*Lenticels*.—Approximate Number Per Square Inch: 5. Color: Light yellowish brown [76. l.yBr]. Average Size: ¼" [6.4 mm.] in length. The width is typically one fourth as much as the length. Shape: Eye-shaped.

Branches:

*Size*.—Slim, diameter of the lowest side hanger is ⅞" [22 mm.] measured 6" from the central leader.

*Texture*.—Smooth on first and second year wood, increasing in roughness with age.

*Color*.—1st Year Wood Topside: Grayish red [19. gy.R]. 1st Year Wood Underside: Brilliant yellow green [116. brill.YG]. 2nd Year Wood: A Moderate yellowish brown [77. m.yBr].

*Lenticels*.—Number Per Square Inch: About 25 on second year wood. Color: Light grayish yellowish brown [79. l.gy.yBr]. Average Size: Small, 1/32" [0.8 mm.] in length. The width is typically one fourth as much as the length. Shape: Eye-shaped.

Leaves:

*Size*.—Medium. Average Length: 5⅛" [130.2 mm.]. Average Width: 1⅝" [41.3 mm.].

*Arrangement*.—Alternate.

*Thickness*.—Medium.

*Form*.—Elliptical.

*Apex*.—Acuminate.

*Base*.—Acute to rounded.

*Surface*.—Smooth on both sides.

*Color*.—Dorsal Surface: Moderate olive green [125. m.OlG]. Ventral Surface: Moderate yellow green [120. m.YG].

*Red midvein*.—Absent.

*Margin*.—Finely serrate.

*Venation*.—Pinnately net veined.

*Petiole*.—Average Length: 7/16" [11.1 mm.]. Average Thickness: 1/16" [1.6 mm.]. Color: Light yellow green [119. l.YG].

*Stipules*.—Number: 2 per leaf, up to 6 per growing tip. Average Length: 5/16" [7.9 mm.]. Color: Very yellow green [115. v.YG] becoming Moderate brown [58. m.Br] with age.

*Glands*.—Number: 2 to 6 per leaf. Position: First pair is at the petiole and base of blade. Form: Reniform. Size: Small, about 1/32" [0.8 mm.] in length, about 1/64" [0.4 mm.] in width. Color: Brilliant yellow green [116. brill.YG].

*Leaf buds*.—Pointed.

Flower buds:

*Hardiness*.—Hardy, with respect to central California blooming season.

*Diameter*.—Typically ⅜" [9.5 mm.] 1 week before bloom.
*Length*.—Typically ⅝" [15.9 mm.] 1 week before bloom.
*Form*.—Not appressed.
*Surface*.—Pubescent.
*Tip color*.—Light purplish pink [249. l.pPk].

Flowers: Perfect, complete, perigynous, usually a single pistil, about thirty stamens, five sepal and petal locations alternately positioned.
*Type*.—Showy, large.
*Average flower diameter*.—1 13/16" [46.0 mm.].
*Average flower depth*.—7/16" [11.1 mm.] when fully open.
*Average pedicel length*.—⅛" [3.2 mm.].
*Number of petals*.—Mostly five, extra petal fragments common, double blossoms occasionally observed.
*Petal shape*.—Circular to oval.
*Petal margin*.—Entire, quite wavy.
*Average petal diameter*.—11/16" [17.5 mm.].
*Average petal length*.—¾" [19.1 mm.].
*Petal apex*.—Rounded.
*Petal base*.—Rounded to somewhat truncate.
*Petal color*.—Light pink [4. l.Pk] toward the apex, Deep pink [3. deep Pk] toward the base on both sides.
*Anther color*.—Moderate reddish orange [37. m.rO] at bloom onset.
*Pollen*.—Anthers produce an abundance of Brilliant yellow [83. brill.Y] pollen.
*Stigma color*.—Light yellow green [119. l.YG].
*Stigma position*.—Typically located about even with the nearby anthers.
*Ovary*.—Pubescent.
*Sepal color*.—Dark purplish red [259. d.pR] on the outer surface. The inner surface is a somewhat translucent Pinkish white [9. pkWhite] with both Grayish purplish red [262. gy.pR] and Vivid yellow green [115. v.YG] areas visible.
*Sepal length*.—¼" [6.4 mm.].
*Sepal width*.—¼" [6.4 mm.].
*Sepal apex*.—Rounded to elliptical to match the sepal length and width.
*Sepal margin*.—Fairly smooth.
*Average pistil length*.—⅝" [15.9 mm.].
*Average stamen length*.—9/16" [14.3 mm.].
*Fragrance*.—Moderate.
*Blooming period*.—Early compared to other varieties, two days before 'May Princess' (U.S. Plant Pat. No. 18,771) peach.
*Onset of bloom*.—One percent on Feb. 4, 2015.
*Date of full bloom*.—Feb. 14, 2015.
*Duration of bloom*.—One to two weeks, dependent on ambient temperature.
*Bloom density*.—Heavy.
*Number per cluster*.—1 to 3 with single flowers most common.

FRUIT

Maturity when described: Firm ripe, May 20, 2015.
Date of first picking: May 15, 2015.
Date of last picking: May 25, 2015.
Size: Uniform, large.
*Average diameter axially*.—2¾" [69.9 mm.].
*Average diameter across suture plane*.—3¼" [82.6 mm.].
*Average diameter across cheek plane*.—3¼" [82.6 mm.].
*Typical weight*.—9.2 ounces [261 grams].

Form: Uniform, oblate, compressed axially, mostly symmetrical.
*Longitudinal section form*.—Oblate.
*Axial view*.—Round.

Suture: Extends from the base to just beyond the pistil point with a slight depression beyond pistil point.
*Near the base*.—A sharp groove.
*Along the side*.—A shallow trough.
*Near the apex*.—A shallow groove.

Ventral surface: Rounded, lipped toward the apex on both sides.
Lips: Fairly equal.

Cavity: Flaring, elongated in the suture plane, suture showing on both sides. Brilliant orange yellow [67. brill.OY] stem markings present.
*Depth*.—¾" [19.1 mm.].
*Breadth*.—1⅜" [34.9 mm.].

Base: Truncate.
Apex: Rounded to slightly truncate, never mammiform.
Pistil point: Apical, negligible length, depressed within the suture.
Stem: Medium.
*Average length*.—⅜" [9.5 mm.].
*Average width*.—3/16" [4.8 mm.].

Skin:
*Thickness*.—Medium.
*Surface*.—Pubescent.
*Tenacity*.—Tenacious to the flesh.
*Astringency*.—Moderate.
*Tendency to crack*.—None observed.
*Color*.—Very dark red [17. v.d.R] tiger striping over a Moderate red [15. m.R] background with a slight amount of Pale orange yellow [73. p.OY] areas if sun protected by a limb or leaf.
*Down*.—Moderate, short, does not roll up when rubbed.

Flesh:
*Color*.—Brilliant yellow [83. brill.Y] with very slight Moderate pink [5. m.Pk] flecking which increases with maturity.
*Surface of pit cavity*.—Covered with Light yellow [86. l.Y] broken fibers when twisted away from the stone.
*Amygdalin*.—Moderate.
*Juice*.—Moderate, rich.
*Texture*.—Firm, non-melting.
*Fibers*.—Abundant, fine, tough.
*Ripens*.—Fairly even.
*Flavor*.—Classic peach flavor, medium acidity, moderately sweet, typically 13 brix.
*Aroma*.—Moderate.
*Eating quality*.—Very good.

STONE

Type: Clingstone.
Form: Elliptical.
Hilum: Narrow, oblong.
Base: Rounded to somewhat truncate.
Apex: Acuminate.

Sides: Equal.
Tip: Sharp.
Surface: Pitted throughout, absent of furrows and ridges except along the dorsal fin and ventral edge.
Ridges: None.
External color: Pale orange yellow [73. p.OY] when first removed.
Pit wall color when cracked: Pale orange yellow [73. p.OY].
Cavity surface color: Light yellowish brown [76. l.yBr].
Average pit wall thickness: ¼" [6.4 mm.].
Average length: 1⅞" [47.6 mm.].
Average width: 1" [25.4 mm.].
Average breadth: ¾" [19.1 mm.].
Tendency to split: Very slight.
Kernel:
*Form*.—Oval.
*Skin color*.—Light yellow [86. l.Y].
*Pellicle color*.—Yellowish gray [93. yGy].
*Vein color*.—Moderate yellow [87. m.Y].
*Taste*.—Bitter.
*Viable*.—Only with embryo rescue techniques.
*Average width*.—7/16" [11.1 mm.].
*Average length*.—11/16" [17.5 mm.].
*Amygdalin*.—Abundant.

USE

Market: Fresh market and long distance shipping.
Keeping quality: Good, fruit quality observed to remain in good condition after 17 days in standard cold room at 36° Fahrenheit [2° Celsius].
Shipping quality: Good.
Resistance to insects: Not tested.
Resistance to diseases: Not tested.

OTHER NOTES

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, that is most similar to 'Spring Princess' (U.S. Plant Pat. No. 17,750) peach by being self-fertile, by having a low chilling requirement, by having a large blossom, by blooming in the early season and by producing peaches that are mostly red in skin color, yellow in flesh color, oblate in shape, clingstone in type, large in size, and very good in flavor, but is distinguished therefrom by having a smaller and less vigorous tree, by having reniform instead of globose glands, and by producing fruit that is non-melting instead of melting in texture, that has a bitter instead of sweet kernel, and that ripens about five days later.

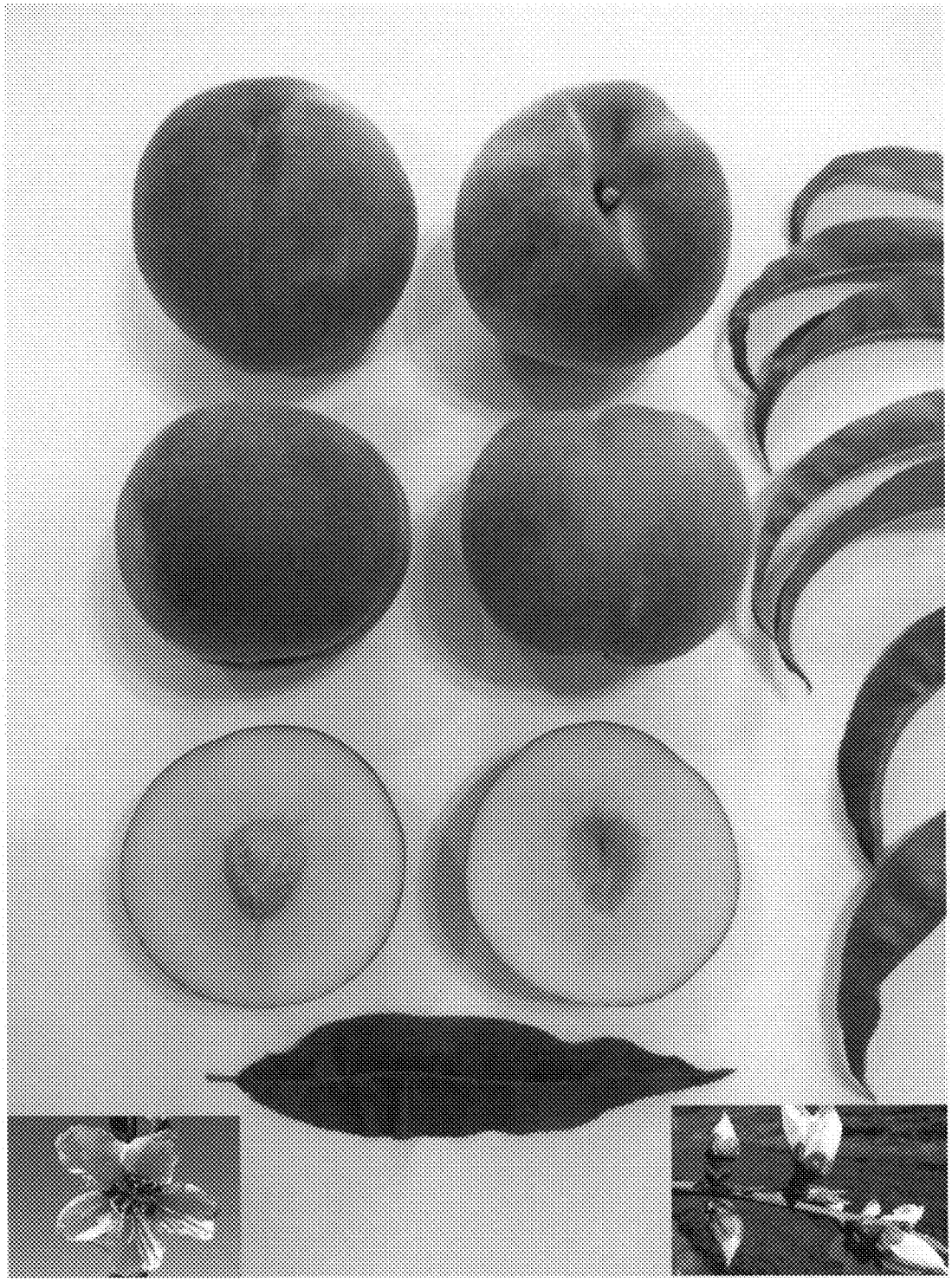

* * * * *